United States Patent [19]
Wheeler

[11] Patent Number: 6,165,479
[45] Date of Patent: Dec. 26, 2000

[54] DISPERSIONS COMPRISING AN OIL-BASED BILIQUID FOAM AND AN AQUEOUS GEL

[75] Inventor: Derek Alfred Wheeler, Dorking, United Kingdom

[73] Assignee: Disperse Technologies Limited, Falmouth, United Kingdom

[21] Appl. No.: 09/142,397

[22] PCT Filed: Mar. 6, 1997

[86] PCT No.: PCT/GB97/00608

§ 371 Date: Sep. 4, 1998

§ 102(e) Date: Sep. 4, 1998

[87] PCT Pub. No.: WO97/32559

PCT Pub. Date: Sep. 12, 1997

[30]  Foreign Application Priority Data

Mar. 8, 1996 [GB] United Kingdom .................... 9604972
Apr. 1, 1996 [GB] United Kingdom .................... 9606869

[51] Int. Cl.[7] ............................... A61K 9/00; A61K 7/00; A61K 7/06; A61K 7/075
[52] U.S. Cl. .................. 424/400; 424/70.12; 424/70.16; 424/70.19; 424/401; 514/938
[58] Field of Search .................................. 424/401, 70.1, 424/70.16, 70.12, 70.19, 400; 514/938

[56]  References Cited

U.S. PATENT DOCUMENTS 4,040,857  8/1977  Lissant .
4,486,333  12/1984  Sebba .
4,606,913  8/1986  Aronson et al. .
4,999,198  3/1991  Barnett et al. .

FOREIGN PATENT DOCUMENTS 0392426  10/1990  European Pat. Off. .
2618351  1/1989  France .
2720934  12/1995  France .
4425268  1/1996  Germany .

*Primary Examiner*—Diana Dudash
*Assistant Examiner*—Alysia Berman
*Attorney, Agent, or Firm*—Fish & Richardson P.C.

[57]  ABSTRACT

A stable dispersion comprising an oil-based biliquid foam and an aqueous gel which is suitable for use in the cosmetics, pharmaceuticals and other industries. The biliquid foam comprises a dispersion of oil droplets in an aqueous medium stabilized by only a small amount of surfactant, thus keeping the level of skin irritation low. The gel may be a colloidal aqueous gel.

8 Claims, No Drawings

DISPERSIONS COMPRISING AN OIL-BASED BILIQUID FOAM AND AN AQUEOUS GEL

BACKGROUND OF THE INVENTION

This invention relates to new dispersions, and more particularly it relates to stable dispersions of water-insoluble substances in aqueous media which are based on biliquid foams entrapped in aqueous gels.

Dispersions of oils and oil-soluble materials in aqueous media are widely used in many industries, in particular the cosmetics, food, paints, pharmaceuticals and printing industries. Such dispersions typically depend for their stability on the presence of surface-active chemicals, generally known as emulsifying agents or surfactants, which migrate to the oil-water interface which surrounds each individual suspended oil droplet, and prevent said droplet from coalescing with other droplets with which it may come into contact. Such dispersions are generally known as emulsions and typically contain, depending on the chemical nature and concentration of the components of the emulsion, from 3 to 10% by weight of surfactant.

A disadvantage of the presence of surfactants in emulsions, particularly in the cosmetics and pharmaceuticals industries, is their potential, to a greater or lesser extent, to cause skin irritation. This arises from the physico-chemical nature of all surfactant molecules, especially from their ability to combine with skin lipids, and is concentration-dependent. It is therefore essential, in well-formulated cosmetic and pharmaceutical products, to use the minimum surfactant concentration consistent with providing stability of the emulsion, but said minimum concentration in practical terms is necessarily fairly high.

A further disadvantage of the presence of surfactants in emulsions is their detrimental effect on the efficacy of many preservatives, which are essential in emulsion formulations to prevent the growth of unwanted organisms such as bacteria, yeasts and other fungi. As a result, in the presence of surfactants, levels of preservatives need to be higher than they might otherwise be. The disadvantage is compounded because the preservatives themselves are skin-sensitizing, and higher levels thereof exacerbate the skin problems.

Apart from the problem with surfactants, many emulsions known for use as cosmetics or pharmaceuticals contain, in order to produce stable formulations of desired viscosity, fatty chemicals such as cetyl or stearyl alcohol, glyceryl stearate, petroleum, or waxes, either natural (for example beeswax, candelilla wax or carnauba wax) or synthetic (such as microcrystalline or paraffin wax). These form a fatty, pore-clogging, occlusive film on skin which users find abhorrent.

By virtue of the oily materials which they contain, many emulsions, particularly those used as skin cleansers, have to be removed from the skin by wiping with tissue material, and cannot be rinsed from the skin by aqueous means and remain effective, and these emulsions are not liked by their users for this reason.

An alternative cosmetic or pharmaceutical product for topical use comprises a liquid or gel wherein the gelling agent is either entirely water-based, or alternatively entirely oil-based. The disadvantage of the former type is that, despite feeling light and refreshing in use, it cannot deliver oil-soluble or oil-dispersible materials to the skin, and the disadvantage of the latter type is the unpleasantness in use, as explained in the previous paragraph.

There are also known aqueous gel products designed for cleaning and conditioning hair and skin, which comprise high levels of surfactants, either with or without additional gelling agents. Such products are known as hair shampoos, body shampoos, bath or foam gels, bubble or foam baths and products of similar descriptions. The primary purpose of such products is as hair or skin cleansers, but a secondary objective is to provide a lasting pleasant feel to the hair or skin, and to provide a lustrous shine to the hair, these effects being generally known as "conditioning". Oils used in skin care products, particularly silicones and their derivatives, are amongst the most effective conditioning agents but it is difficult to incorporate these into shampoos and similar products in sufficient quantities to provide an adequate conditioning effect, without destroying gel viscosity or foaming effect.

Dispersions of oil droplets in aqueous media are known which are stabilized by thin films containing low levels of surfactants, and these films are generally known as "biliquid foams". These foams are not emulsions (Sebba, Chemistry and Industry, 1984, pp 367–372) and may contain dispersed oil content of up to 95% by volume. They are insufficiently stable to form useable cosmetic or pharmaceutical products because the foam breaks at the air-water interface and deposits a layer of oil on the surface which, for reasons set out above, is unacceptable to the user.

The present invention is addressed to formulations for use in the cosmetics, pharmaceuticals and other industries which are based on biliquid foams, but which do not possess the disadvantages set out above and in particular are less skin-irritant by virtue of their requirement for only low levels of surfactants, and as a consequence only low levels of preservatives.

SUMMARY OF THE INVENTION

The invention comprises a stable dispersion comprising an oil-based biliquid foam an d an aqueous gel which may be a colloidal aqueous gel.

The oil-based biliquid foam will generally comprise between approximately 1 and 80%, preferably 1 and 50%, by weight of the total formulation, and the aqueous gel will comprise between approximately 20 and 99%, preferably 50 and 99% thereof. A surfactant to stabilize the formulation may comprise between 0.05 and 0.5%, and preferably between 0.05 and 0.3%, thereof. The active ingredient if there is such can be present in either the aqueous phase or the oily phase.

Oils used in the biliquid foam will in general be liquid at room temperature and may be, for example, a cyclomethicone, dimethicone, dimethiconol, dimethicone copolyol, an emollient ester such as isopropyl isostearate, lanolate, myristate or paimitate, or octyl palmitate, a glyceride such as avocado oil, coconut oil, soybean oil or sunflower oil, or a caprelic/capric triglyceride, a lanolin oil, mineral oil or natural oil, or olepl alcohol, or any other oil generally known for this purpose.

DETAILED DISCLOSURE

The aqueous phase will in general comprise a colloidal polymer or gum suspended in water, at a concentration of between 0.05 and 20%, more particularly 0.2 to 1%, by weight. Suitable polymers or gums are, for example, alginate gums or their salts, guar gum, locust bean gum, xanthane gum, gum acacia, gelatin, hydroxymethylcellulose or its sodium salt, hydroxyethyl-cellulose, hydroxypropylcellulose, carboxymethylcellulose, bentonites, magnesium aluminum silicates, "Carbomers" (salts of cross-linked polymers of acrylic acid), or glyceryl polymethacrylates or their dispersions in glycols, or any appropriate mixture of any of these polymers and gums. Preferred gelling agents are those which confer plastic behaviour on the aqueous phase, that is, under their influence, any shear stress applied to the product must attain a minimum yield value before any liquid flow takes place.

The aqueous phase may also contain water-soluble or water-dispersible materials commonly used in cosmetic or pharmaceutical formulations, such as an alcohol (for example ethanol or propanol), a glycol (for example propylene glycol), glycerin, an aqueous or alcoholic extract of a natural plant, a conditioning agent, a humectant or any other water-soluble material generally known for this purpose.

The formulation may contain, as described above, a low level of a surfactant which may be, for example:

a cationic surfactant such as an amidoamine, a quaternary ammonium compound or a sulphonium salt;

an amphoteric surfactant such as an acylaminoacid, an N-substituted alkylamine, an N-alkyl-β-aminopropionate, an N-alkylbetaine, an alkylimidazoline or a sulphobetaine;

an anionic surfactant such as an acyl-lactate, N-acylsarcosinate, alkyl-carboxylate (either mono- or polyvalent), alkyl ether carboxylate, N-alkyl-glutamate, fatty acid-peptide condensate, phosphated ethoxylated alcohol, alkyl sulphate, ethoxylated alkyl sulphate, alpha-olefin sulphonate or ester-linked sulphonate;

a nonionic surfactant such as an alkanolamide, amine oxide, ester of a polyhydric alcohol (for example an ester of an ethylene, diethylene or propylene glycol, or glycerol or a polyglycerol, or sorbitan, glucose or sucrose), a polyoxyethylene or polyoxypropylene derivative of an alcohol, amide or ester, or a polyoxyethylene/polyoxypropylene block copolymer; or a suitable compatible mixture of these surfactants.

The formulation may also contain an antimicrobial agent (preservative) such as an ester of p-hydroxybenzoic acid, formalin or imidazolidinylurea, or any other such product generally known for use in the cosmetics or pharmaceutical industries. It may further contain an opacifying or pearlising agent, for example an alkanolamide of a higher fatty acid such as stearic or behenic acid, a glycol mono- or distearate or palmitate, a propyleneglycol monostearate or palmitate, a fatty alcohol such as cetyl or stearyl alcohol, an emulsion of a vinyl polymer or latex, an insoluble salt, such as a calcium, magnesium or zinc salt, of stearic acid, finely dispersed zinc and/or titanium oxide, a titanium coated mica, magnesium aluminum silicate or any other such product generally known for use in the cosmetics or pharmaceutical industries. It may still further contain an antioxidant, a sequestering agent, such as ethylenediamine tetraacetic acid (EDTA) or a salt or polyphosphate thereof, a colouring agent (for example an acceptable dye or pigment), flavouring agent or perfume, or any other such agent generally known for use in these industries.

One advantage of the formulation of the present invention over those of the prior art is that it can deliver oil-soluble products to the skin without giving rise to the unacceptable layer of oil formed, as explained above, by the prior art formulations. A second advantage is that the formulation of the present invention may be rinsed from the skin by aqueous means and still remain effective.

According to a further Feature of the invention there is provided a cleansing and conditioning formulation which comprises a conventional hair or skin cleansing formulation to which is added a biliquid foam.

A suitable conventional hair or skin cleansing formulation is, for example, a hair or body shampoo or a bath or shower gel which will generally consist of an aqueous fluid containing between 4 and 18% by weight of a primary surfactant (for example an alkyl ether sulphate), between 2 and 15% by weight of a coactive surfactant (for example an alkyl betaine) and between 0.5 and 5% by weight of a coactive viscosity modifier (for example an alkyl fatty acid alkanolamide), and additionally or alternatively containing between 0.05 and 5% of a gelling agent, for example a cellulose gum, a "Carbomer" or a polyol fatty acid ester. Such a formulation may also contain one or more perfume, colouring agent, stabiliser (for example an antioxidant, a sequestering agent or a UV-absorbing agent) and/or preservative. It is clear from the above description that by the nature of the conventional formulations this kind of dispersion contains a higher proportion of surfactant than those previously described as features of the invention.

The biliquid foam will generally contain an oil-based conditioning agent, for example a mineral oil, an emollient fatty acid ester or a silicone oil or other silicone derivative. The biliquid foam will generally form between 0.5 and 10%, and more particularly between 2 and 5%, of the total formulation. At such a concentration the conditioning properties of the formulation will be enhanced but the foaming and gel viscosity characteristics of the formulation will be retained.

According to a further feature of the invention there is provided a method for the manufacture of a dispersion of the invention which comprises incorporating an oil-based biliquid foam into an aqueous gel. Commonly the aqueous gel will be a conventional aqueous formulation of the appropriate type.

The invention is illustrated but not limited by the following Examples, in which all percentages are expressed by weight:

EXAMPLE 1

A skin-cleansing product

The aqueous phase consists of the following components:

|  | % |
| --- | --- |
| De-ionized water | 95.54 |
| Propylene glycol | 3.00 |
| Triethanolamine | 0.80 |
| Cross-linked polymethacrylate ('Carbopol' 980, B F Goodrich) | 0.50 |
| Methylparaben | 0.08 |
| Imidazolidinylurea ('Germall' 115, Sutton Labs.) | 0.08 |
|  | 100.00 |

The 'Carbopol' was dispersed into the water using a high-shear rotor-stator mixer. The preservatives (methylparaben and imidazolidinylurea) were dissolved in the propylene glycol with gentle warming and the solution was added to the aqueous dispersion. The triethanolamine was added until pH 6.5 was achieved and there was thus obtained a clear aqueous gel.

The biliquid foam consists of the following components:

|  | % |
|---|---|
| Light mineral oil | 90.05 |
| De-ionised water | 9.00 |
| Polyoxyethylene (3) lauryl ether ('Volpo' L3, Croda) | 0.90 |
| Lauryl betaine ('Empigen' BB, Marchon) | 0.05 |
|  | 100.00 |

Air was blown through a mixture of the lauryl betaine and the water to produce a foam, and a mixture of the ethoxylated lauryl ether and the mineral oil was added with gentle stirring. There was thus obtained a biliquid foam of which 30 g was added to 70 g of the aqueous gel to produce a cleansing product. This product has the superficial appearance of a cream but exhibits gel-like characteristics. It is mild and refreshing upon application to the skin, is an effective skin-cleansing agent and may easily be removed from the skin either by wiping with tissue or rinsing with clear tepid water.

EXAMPLE 2

A Conditioning Shampoo

The total composition of the shampoo is as follows:

|  | % |
|---|---|
| 33% Aqueous ammonium lauryl sulphate | 41.0 |
| De-ionised water | 29.8 |
| 30% Aqueous ammonium lauryl ether sulphate | 13.0 |
| 30% Cocamidopropyl betaine | 5.0 |
| 90% Dimethicone biliquid foam | 3.5 |
| Sodium chloride | 3.0 |
| Ethylene glycol distearate | 1.5 |
| Citric acid | 1.0 |
| Coconut diethanolamide | 1.0 |
| Cetostearyl alcohol | 0.5 |
| Fragrance | 0.5 |
| 5-Bromo-5-nitro-1,3-dioxan in propylene glycol ('Bronidox L', Henkel,), used as a preservative | 0.2 |
| Colouring agent | trace |
|  | 100.0 |

The biliquid foam was prepared as described in Example 1 except that dimethicone (Silicone fluid 200/350, Dow Corning), was substituted for the mineral oil. All the above ingredients apart from the fragrance, preservative and colouring agent were mixed together and heated to 70° until a clear viscous mass was formed. The mixture was then stirred and cooled to 40° and the fragrance and preservative were added. The mixture was adjusted to pH 5.5 by the addition of extra citric acid, and to a viscosity of 9,000 centipoise by the addition of extra sodium chloride, and finally a suitable colouring agent was added. There was thus obtained a hair shampoo which was pearly opaque, deeply foaming and left the hair shiny, manageable and feeling well-conditioned.

EXAMPLE 3

A Conditioning Shampoo

The total composition of the shampoo is as follows:

|  | % |
|---|---|
| 33% Aqueous ammonium lauryl sulphate | 41.0 |
| De-ionised water | 20.8 |
| 30% Aqueous ammonium lauryl ether sulphate | 13.0 |
| 30% Cocamidopropyl betaine | 5.0 |
| 90% Dimethicone biliquid foam | 3.5 |
| Cross-linked polymethacrylate (1% 'Carbopol' 980, B F Goodrich, neutralised with triethanolamine) | 10.0 |
| Sodium chloride | 3.0 |
| Ethylene glycol distearate | 1.5 |
| Coconut diethanolamide | 1.0 |
| Cetostearyl alcohol | 0.5 |
| Fragrance | 0.5 |
| 5-Bromo-5-nitro-1,3-dioxan in propylene glycol ('Bronidox L', Henkel,), used as a preservative | 0.2 |
| Colouring agent | trace |
|  | 100.0 |

The biliquid foam was prepared as described in Example 1 except that dimethicone (Silicone fluid 200/350, Dow Corning), was substituted for the mineral oil. All the above ingredients apart from the fragrance, preservative and colouring agent were mixed together and heated to 70° until a clear viscous mass was formed. The mixture was then stirred and cooled to 40° and the fragrance and preservative were added. The mixture was then stirred and adjusted to pH 6.5 by the addition of citric acid, and to a viscosity of 9,000 centipoise by the addition of extra sodium chloride, and finally a suitable colouring agent was added. There was thus obtained a hair shampoo which was pearly opaque, deeply foaming and left the hair shiny, manageable and feeling well-conditioned.

EXAMPLE 4

A Moisturiser

The total composition of the moisturiser is as follows:

|  | % |
|---|---|
| Water | 31.8 |
| Cross-linked polymethacrylate (1% 'Carbopol' 980, B F Goodrich, neutralised with sodium hydroxide) | 37.0 |
| 2% Aqueous hydroxyethylcellulose ('Natrosol' 250HR, Aqualon) | 18.5 |
| 90% Mineral oil biliquid foam | 1.6 |
| 90% Cyclomethicone biliquid foam | 3.5 |
| 90% Isopropyl isostearate biliquid foam | 3.5 |
| 90% Dimethiconol biliquid foam | 1.5 |
| Glycerine | 2.5 |
| Methyldibromoglutaronitrile in phenoxyethanol (preservative) | 0.1 |
|  | 100.0 |

The 'Carbopol' was dispersed in water using a high-shear rotorstator mixer (Silverson) and aqueous 1% sodium hydroxide solution was added until a clear viscous gel with pH 7 was obtained. The 'Natrosol' was similarly dispersed but without the need of sodium hydroxide. All the biliquid foams were prepared as described in Example 1 using mineral oil, cyclomethicone, isopropyl isostearate or dimethiconol as appropriate. All the ingredients were mixed together at room temperature until a smooth, semiviscous white gel was obtained. When applied to the skin the gel spread easily in a light and refreshing manner, was rapidly absorbed without stickiness and produced a smooth moisturised feeling.

EXAMPLE 5

A Toner

The total composition of the toner is:

| | % |
|---|---|
| Water | 79.9 |
| 1% Aqueous 'Carbopol' 980 (neutralised with sodium hydroxide) | 8.0 |
| 90% Cyclomethicone biliquid foam | 6.0 |
| 90% Dimethiconol biliquid foam | 1.0 |
| Glycerine | 5.0 |
| Methyldibromoglutaronitrile in phenoxyethanol (preservative) | 0.1 |
| | 100.0 |

The ingredients were prepared as described in Example 4 and mixed together at room temperature until a uniform slightly cloudy liquid was obtained. When applied to the skin the liquid produced a light, non-greasy refreshing sensation leaving the skin feeling smooth.

EXAMPLE 6

A Moisturising Shower Gel

The total composition of the gel is as follows:

| | % |
|---|---|
| Water | 38.88 |
| 28% Aqueous sodium lauryl ether sulphate | 32.14 |
| 30% aqueous coamidopropylbetaine | 12.38 |
| Lauryl glucoside | 2.25 |
| 90% Dimethicone biliquid foam | 3.50 |
| Polyethylene glycol (PEG-18) glyceryl oleate/cocoate | 0.15 |
| Glycol stearate | 0.30 |
| Ethoxylated stearyl alcohol (Steareth-4) | 0.30 |
| 1% Aqueous 'Carbopol' 980 (neutralised with sodium hydroxide) | 10.00 |
| Methyldibromoglutaronitrile in phenoxyethanol (preservative) | 0.10 |
| | 100.00 |

The 'Carbopol' and biliquid foams were prepared as described in previous examples and the ingredients were mixed together as described in Example 3 until a viscous shower gel having a slightly pearly appearance was obtained. This was cooled to room temperature. When used as a shower gel it gave the skin a pleasant emollient effect during use and after the skin was dried it had a clean, smooth and moisturised feel.

What is claimed is:

1. A stable dispersion comprising an oil-based biliquid foam and an aqueous gel, wherein the oil-based biliquid foam constitutes from 1 to 80% by weight of the dispersion, the aqueous gel constitutes frolic 20 to 99% by weight of the dispersion, and said dispersion also includes a surfactant.

2. A dispersion as claimed in claim 1 wherein the biliquid foam comprises from 1 to 50% by weight of the dispersion and the aqueous gel comprises from 50 to 99% by weight of the dispersion.

3. A dispersion as claimed in claim 1 wherein the surfactant comprises from 0.05 to 0.5% by weight thereof.

4. A dispersion as claimed in claim 3 wherein the surfactant comprises from 0.05 to 0.3% by weight thereof.

5. A dispersion as claimed in claim 1 which comprises as the aqueous gel an aqueous fluid which contains one or more components selected from the group consisting of a primary surfactant, a coactive surfactant, a coactive viscosity modifier and a gelling agent.

6. A dispersion as claimed in claim 5 wherein the biliquid foam comprises from 1 to 10% by weight of the dispersion.

7. A dispersion as claimed in claim 6 wherein the biliquid foam comprises from 2 to 5% by weight of the dispersion.

8. A method for the manufacture of a stabilised dispersion as claimed in claim 1 which comprises incorporating an oil-based biliquid foam into an aqueous gel.

\* \* \* \* \*

UNITED STATES PATENT AND TRADEMARK OFFICE
CERTIFICATE OF CORRECTION

PATENT NO.    : 6,165,479
DATED         : DECEMBER 26, 2000
INVENTOR(S)   : DEREK ALFRED WHEELER

It is certified that error appears in the above-identified patent and that said Letters Patent is hereby corrected as shown below:

At column 8, line 22, delete "frolic" and insert --from--.

Signed and Sealed this

Fifteenth Day of May, 2001

*Attest:*

NICHOLAS P. GODICI

*Attesting Officer*    *Acting Director of the United States Patent and Trademark Office*